US 8,013,197 B2

(12) United States Patent
Peterson et al.

(10) Patent No.: US 8,013,197 B2
(45) Date of Patent: Sep. 6, 2011

(54) ABSORPTION AND CONVERSION OF ACETYLENIC COMPOUNDS

(75) Inventors: Edward R. Peterson, Pearland, TX (US); Sean C. Gattis, Sugar Land, TX (US)

(73) Assignee: Synfuels International, Inc., Dallas, TX (US)

( * ) Notice: Subject to any disclaimer, the term of this patent is extended or adjusted under 35 U.S.C. 154(b) by 998 days.

(21) Appl. No.: 11/346,036

(22) Filed: Feb. 2, 2006

(65) Prior Publication Data

US 2007/0021637 A1 Jan. 25, 2007

Related U.S. Application Data

(60) Provisional application No. 60/654,651, filed on Feb. 18, 2005.

(51) Int. Cl.
*C07C 5/09* (2006.01)

(52) U.S. Cl. ........ 585/259; 585/250; 585/258; 585/260; 585/261; 585/264; 585/271; 585/273; 585/275; 585/277; 585/800; 585/833; 585/864; 585/865; 585/300; 585/301

(58) Field of Classification Search .................. 585/259, 585/258, 260, 261, 275, 833, 841, 265, 250, 585/264, 271, 277, 300, 301, 800, 864, 868
See application file for complete search history.

(56) References Cited

U.S. PATENT DOCUMENTS

| | | | |
|---|---|---|---|
| 2,091,114 A | 8/1937 | Daudt | |
| 2,525,210 A | 10/1950 | Del Camp | |
| 3,342,891 A | 9/1967 | Poons et al. | |
| 3,389,189 A | 6/1968 | Hirayama et al. | |
| 3,541,178 A | 11/1970 | Nettesheim | |
| 3,663,394 A | 5/1972 | Kawahara | |
| 3,697,612 A | 10/1972 | Maniero et al. | |
| 3,703,460 A | 11/1972 | Shair et al. | |
| 3,755,488 A | 8/1973 | Johnson et al. | |
| 3,842,137 A | 10/1974 | Libers et al. | |
| 4,014,947 A | 3/1977 | Volodin et al. | |
| 4,128,595 A | 12/1978 | Montgomery | |
| 4,137,267 A | 1/1979 | Reid et al. | |
| 4,184,322 A | 1/1980 | Paull et al. | |
| 4,256,565 A | 3/1981 | Friedman et al. | |
| 4,277,313 A | 7/1981 | Mehra et al. | |
| 4,288,408 A | 9/1981 | Guth et al. | |
| 4,309,359 A | 1/1982 | Pinto | |
| 4,323,482 A | 4/1982 | Stiles et al. | |

(Continued)

FOREIGN PATENT DOCUMENTS

EP 564328 10/1993

(Continued)

OTHER PUBLICATIONS

A. Molnar, et. al, Journal of Molecular Catalysis A: Chemical, 173 (2001), 185-221.*

(Continued)

*Primary Examiner* — In Suk Bullock
*Assistant Examiner* — Bradley Etherton
(74) *Attorney, Agent, or Firm* — Porter Hedges LLP (57) ABSTRACT

A method for the absorption of alkynes and diolefins from an ethylene or propylene containing stream with conversion to alkenes by catalytic hydrogenation in a solvent over a fixed bed comprising a supported catalyst.

20 Claims, 2 Drawing Sheets

U.S. PATENT DOCUMENTS

| | | | |
|---|---|---|---|
| 4,336,045 A | 6/1982 | Fisher et al. | |
| 4,337,329 A | 6/1982 | Kubo et al. | |
| 4,404,124 A | 9/1983 | Johnson et al. | |
| 4,424,401 A | 1/1984 | White et al. | |
| 4,469,907 A | 9/1984 | Araki et al. | |
| 4,484,015 A | 11/1984 | Johnson et al. | |
| 4,513,164 A | 4/1985 | Olah | |
| 4,517,395 A | 5/1985 | Obenaus et al. | |
| 4,547,600 A | 10/1985 | Cosyns et al. | |
| 4,571,442 A | 2/1986 | Cosyns et al. | |
| 4,575,383 A | 3/1986 | Lowther et al. | |
| 4,599,479 A | 7/1986 | Okamoto et al. | |
| 4,655,904 A | 4/1987 | Okamoto et al. | |
| 4,704,493 A | 11/1987 | Devries et al. | |
| 4,704,496 A | 11/1987 | Paparizos et al. | |
| 4,705,906 A | 11/1987 | Brophy et al. | |
| 4,705,908 A | 11/1987 | Gondouin | |
| 4,727,207 A | 2/1988 | Paparizos et al. | |
| 4,754,091 A | 6/1988 | Jezi et al. | |
| 4,822,940 A | 4/1989 | Leff et al. | |
| 4,906,800 A | 3/1990 | Henry et al. | |
| 4,982,032 A | 1/1991 | Winzenburg et al. | |
| 5,012,028 A | 4/1991 | Gupta et al. | |
| 5,036,032 A * | 7/1991 | Iglesia et al. | 502/260 |
| 5,059,732 A | 10/1991 | Cosyns et al. | |
| 5,068,486 A | 11/1991 | Han et al. | |
| 5,118,893 A | 6/1992 | Timmons et al. | |
| 5,131,993 A | 7/1992 | Suib et al. | |
| 5,227,553 A | 7/1993 | Polanek et al. | |
| 5,254,781 A | 10/1993 | Calamur et al. | |
| 5,277,773 A | 1/1994 | Murphy | |
| 5,288,935 A | 2/1994 | Alario et al. | |
| 5,322,549 A * | 6/1994 | Hayes | 95/45 |
| 5,356,851 A | 10/1994 | Sarrazin et al. | |
| 5,414,170 A | 5/1995 | McCue et al. | |
| 5,504,268 A | 4/1996 | van der Aalst et al. | |
| 5,587,348 A | 12/1996 | Brown et al. | |
| 5,589,600 A | 12/1996 | Fischer et al. | |
| 5,676,293 A | 10/1997 | Farris | |
| 5,749,937 A | 5/1998 | Detering et al. | |
| 5,847,250 A | 12/1998 | Flick et al. | |
| 5,856,262 A | 1/1999 | Flick et al. | |
| 5,866,734 A | 2/1999 | Flick et al. | |
| 5,886,056 A | 3/1999 | Hershkowitz et al. | |
| 5,925,799 A * | 7/1999 | Stanley et al. | 585/259 |
| 5,935,056 A | 8/1999 | Kerin et al. | |
| 5,935,293 A | 8/1999 | Detering et al. | |
| 5,935,489 A | 8/1999 | Hershkowitz et al. | |
| 5,938,975 A | 8/1999 | Ennis et al. | |
| 5,981,818 A | 11/1999 | Purvis et al. | |
| 6,015,933 A | 1/2000 | Abrevaya et al. | |
| 6,090,977 A | 7/2000 | Hefner et al. | |
| 6,127,310 A | 10/2000 | Brown et al. | |
| 6,127,588 A * | 10/2000 | Kimble et al. | 585/260 |
| 6,130,260 A | 10/2000 | Hall et al. | |
| 6,179,996 B1 * | 1/2001 | Baker et al. | 208/103 |
| 6,187,226 B1 | 2/2001 | Detering et al. | |
| 6,255,548 B1 | 7/2001 | Didillon et al. | |
| 6,281,160 B1 | 8/2001 | Basset et al. | |
| 6,323,247 B1 | 11/2001 | Hall et al. | |
| 6,340,429 B1 * | 1/2002 | Minkkinen et al. | 208/87 |
| 6,350,717 B1 | 2/2002 | Frenzel et al. | |
| 6,365,790 B2 | 4/2002 | Reimer et al. | |
| 6,365,792 B1 | 4/2002 | Stapf et al. | |
| 6,375,892 B2 | 4/2002 | Thomas | |
| 6,395,952 B1 | 5/2002 | Barchas | |
| RE37,853 E | 9/2002 | Detering et al. | |
| 6,465,391 B1 * | 10/2002 | Cheung et al. | 502/330 |
| 6,509,292 B1 | 1/2003 | Blankenship et al. | |
| 6,518,476 B1 | 2/2003 | Culp et al. | |
| 6,566,573 B1 | 5/2003 | Bharadwaj et al. | |
| 6,578,378 B2 | 6/2003 | Kaiser et al. | |
| 6,596,912 B1 | 7/2003 | Lunsford et al. | |
| 6,602,920 B2 | 8/2003 | Hall et al. | |
| 6,822,127 B2 * | 11/2004 | Dai et al. | 585/259 |
| 2003/0021746 A1 | 1/2003 | Fincke et al. | |
| 2003/0105378 A1 | 6/2003 | Satek et al. | |
| 2007/0149835 A1 * | 6/2007 | Cheung et al. | 585/258 |

FOREIGN PATENT DOCUMENTS

EP          564329          10/1993

OTHER PUBLICATIONS

"Aprotic solvent" in Hawley's Condensed Chemical Dictionary (14th edition), John Wiley & Sons, (2002).*

International Search Report dated Feb. 28, 2008.

* cited by examiner

ABSORPTION AND CONVERSION OF ACETYLENIC COMPOUNDS

CROSS-REFERENCE TO RELATED APPLICATIONS

The present application claims the benefit of 35 U.S.C. 111(b) provisional application Ser. No. 60/654,651 filed Feb. 18, 2005, and entitled Absorption and Conversion of Acetylenic Compounds.

STATEMENT REGARDING FEDERALLY SPONSORED RESEARCH OR DEVELOPMENT

Not Applicable.

BACKGROUND OF THE INVENTION

1. Field of the Invention

This invention relates to the absorption of acetylenic and multi-ene containing chemicals from an ethylene or propylene containing stream with conversion to more saturated analogs by catalytic hydrogenation. More particularly, this invention relates to a method for converting alkynes and diolefins alkenes by catalytic hydrogenation in a solvent over a fixed bed comprising a supported catalyst.

2. Description of the Related Art

Numerous patents teach hydrogenation of acetylenic and/or diolefinic compounds in the gas phase. U.S. Pat. No. 5,587,348 describes hydrogenation of $C_2$ to $C_{10}$ alkynes contained in comparable streams of like alkenes over a supported palladium catalyst containing fluoride and at least one alkali metal. Examples show hydrogenation of low concentrations of acetylene, below 1%, converted to ethylene in a gas comprising methane and ethylene at 200 psig (about 13.8 $bar_g$) and 130° F. (54° C.) and 180° F. (82° C.). Care was taken to avoid heating the gas to a runaway temperature, wherein at least 4.5% of the ethylene would be converted to ethane and the temperature would become uncontrollable, which varied from about 70° (21° C.) to 100° F. (38° C.) above the minimum temperature that would reduce the acetylene concentration to acceptable levels.

U.S. Pat. No. 6,127,310 by Brown et al. teaches that the selective hydrogenation of alkynes, which frequently are present in small amounts in alkene-containing streams (e.g., acetylene contained in ethylene streams from thermal alkane crackers), is commercially carried out in the presence of supported palladium catalysts. In the case of the selective hydrogenation of acetylene to ethylene, preferably an alumina-supported palladium/silver catalyst in accordance with the disclosure in U.S. Pat. No. 4,404,124 and its division U.S. Pat. No. 4,484,015, is used. The operating temperature for this hydrogenation process is selected such that essentially all acetylene is hydrogenated to ethylene (and thus removed from the feed stream) while only an insignificant amount of ethylene is hydrogenated to ethane (to minimize ethylene losses and to avoid a runaway reaction which is difficult to control, as has been pointed out in the above-identified patents).

U.S. Pat. No. 6,350,717 describes use of a palladium-silver supported catalyst to hydrogenate acetylene to ethylene in the gas phase and propyne and/or propadiene to propylene in the gas or mixed phase. The acetylene is present at levels of 1% in a stream of ethylene.

U.S. Pat. No. 5,856,262 describes use of a palladium catalyst supported on potassium doped silica wherein acetylene ranging in concentration from 0.01% to 5% in blends of ethylene and ethane is converted to ethylene in the gas phase.

U.S. Pat. No. 6,509,292 describes use of a palladium-gold catalyst wherein acetylene contained in a stream of principally ethylene, hydrogen, methane, ethane and minor amounts of carbon monoxide is converted to ethylene in the gas phase. This patent describes two types of acetylene hydrogenation—front end, where all the gas produced is exposed to the catalyst and tail end, where the components are first separated and a concentrated stream of acetylene or acetylenic compounds is hydrogenated.

U.S. Pat. No. 6,578,378 describes a complex process for purification of ethylene produced from pyrolysis of hydrocarbons. At the top of the de-ethanizer the vapor of the column distillate is treated directly in an acetylene hydrogenation reactor, the effluent containing virtually no acetylene being separated by a distillation column called a de-methanizer, into ethylene- and ethane-enriched tail product. The vapor containing acetylene is exposed to selective hydrogenation to reduce acetylene content of the principally ethylene gas or treated with solvent to remove it and preserve it as a separate product. In all cases the acetylene content of the pyrolysis gas contained less than 1.5 mol % acetylene.

Several patents teach hydrogenation of acetylenic compounds in the liquid phase. U.S. Pat. No. 3,755,488 describes the use of an aprotic solvent, including DMF, NMP and sulfolane, used to absorb acetylene preferentially from a gas stream composed primarily of ethylene and thereafter to subject that solvent containing absorbed acetylene to hydrogenation in the liquid phase. Selectivity is shown as high as 95% and conversion is as high as 93% when using a 5% Pd on alumina catalyst. This reaction ran for approximately 6 minutes using DMF as the aprotic solvent. The short useful reaction times of the catalyst that contained a large quantity of expensive palladium present serious impediments to industrial application.

U.S. Pat. No. 4,128,595 presents a process wherein gaseous acetylene or acetylene group containing compounds are contacted with hydrogen via an inert saturated liquid hydrocarbon stream with hydrogenation occurring over a typical Group VIII metal supported on a catalyst medium. Examples of inert saturated hydrocarbons include various hexanes, decanes and decalin. The process requires the acetylene containing compound and saturated hydrocarbon solvent be fed co-currently into the top of a trickle bed reactor because the solubility of the acetylene-containing compound in the saturated hydrocarbon solvent is poor at reaction conditions. This patent reveals that use of a polar solvent in place of the saturated hydrocarbon will provide inferior results. They show that selectivity in DMF is about 75% and that conversion dropped from 100% to 50% after operation of the reactor for 17 hours.

U.S. Pat. No. 4,571,442 relates to a process whereby acetylene and ethylene are concurrently subjected to hydrogenation over a palladium on alumina catalyst while in the presence of some liquid. The liquid comprises aromatic hydrocarbon and either primary or secondary amine. The purported advantages of using a solvent include better control of the heat released by reaction, improvement of hydrogenation selectivity and improvement of catalyst activity and stability. The results clearly show that hydrogenation of the entire stream results in loss of a substantial amount of the olefin to alkane, although using a liquid to moderate the heat released of hydrogenation may be of interest. Catalyst lifetimes are reportedly 50 hours or more. Disadvantages of using such a solvent mixture include, 1) maintaining the solvent mixture at the desired composition, 2) removal of contaminants derived from the amines, 3) the need to move a large quantity of liquid through the reactor with respect to the quantity of acetylenic and/or diolefinic contaminants contained within the olefin, and 4) the inability of the liquid to separate the reactive gas component from the inactive gas components.

U.S. Pat. No. 6,395,952 describes recovery of olefins from a cracked gas stream using metallic salts and ligand. The cracked gas stream is hydrogenated prior to scrubbing to remove acetylene from the stream.

U.S. Pat. No. 5,414,170 teaches selective hydrogenation of a stream emanating from an olefin plant after operation of a de-propanizer but prior to operation of a de-ethanizer or de-methanizer. The hydrogenation is performed on the mixed-phase propane-rich ethylene stream as well as subsequently on the vapor product. The purpose of this patent is to present a method by which the acetylenes in the front end of an olefin plant process stream are hydrogenated. The propane liquids, initially separated out of the inlet process stream are used later to cool and wash the product of the acetylene hydrogenation reactor by adding them to the acetylene-containing stream during hydrogenation.

French Patent FR 2,525,210 reveals a method for purification of a stream consisting mostly of ethylene with a smaller amount of acetylene contaminant wherein the acetylene is not converted to ethane. The basic concept is to hydrogenate a gas stream short of complete conversion, leaving some acetylene in the gas stream, then absorbing the acetylene in a solvent that extracts the acetylene from the ethylene stream. This extracted acetylene is recycled to the ethylene stream for hydrogenation. Increased conversion to ethylene is claimed.

U.S. Pat. No. 5,847,250 relates to a supported palladium catalyst employing a "promoter" from Groups I or II and the palladium being supported in silica that has been pretreated to contain the promoter. The advantage is that no carbon monoxide is needed to provide increased selectivity because the "selectivity increasing effect of the carbon monoxide is strongly temperature dependent. Large temperature gradients in the catalyst bed therefore have an adverse effect of the selectivity." The reaction is performed in the gas phase in one or more beds with or without intermediate cooling or hydrogen gas addition. Acetylene content ranges from 0.01% to 5%. Reported selectivity ranges from 19 to 56%.

U.S. Pat. No. 4,705,906 presents a new catalyst formulation wherein acetylene is converted by hydrogenation to ethylene in the presence of CO which is in concentrations greater than 1 vol % in a temperature range between 100° C. to 500° C. The catalyst is a zinc oxide or sulfide, which may incorporate chromium, thorium or gallium oxide.

Most providers of acetylenic and diolefinic compound hydrogenation technology, such as Chevron-Phillips, utilize gas phase hydrogenation only. This can be performed directly on the cracked gas, or applied after various clean-up operations are performed (i.e., remove sulfur contaminants) or various gas components (methane, ethane) are separated out. Treating a large stream of gas requires a large reactor and very high catalyst selectivity, since the concentration of the acetylenic and diolefinic compounds is typically 1% or less. Since such catalyst is typically expensive, the conversion needs to be very complete to ensure removal of the undesirable acetylenic and olefinic compounds.

Another common technology is to use a solvent that selectively removes acetylenic and olefinic compounds from the alkene stream, such as Linde AG's DMF absorption process. The acetylenic and diolefinic compounds are not normally hydrogenated because hydrogenation of a concentrated stream of acetylenic and olefinic compounds leads to thermal runaway due to the highly exothermic nature of the hydrogenation reaction in the gas phase.

Other providers, such as Technip, provide both services. However, no commercial process provides absorption coupled with hydrogenation that can be performed in a commercially and economically viable manner as is revealed here.

Although some prior art discloses methods for separating highly unsaturated contaminants from olefinic streams and describes various means and methods for hydrogenating those contaminants to olefins as well as controlling the temperature of the hydrogenation reaction, no economical and integrated method is presently known in the art for the separation of the contaminants from an olefin stream, sequestering these contaminants selectively in an absorbent, hydrogenating those contaminants to olefins while in the absorbent using a catalyst capable of high conversion and selectively for many hours, separation of the hydrogenated compounds from the solvent by ordinary means, and recovery of the hydrogenated product for subsequent use or preferentially recombination with the initially decontaminated olefin stream. The process of the present invention can be performed in a practical and economic manner and overcomes the problems of the prior art.

BRIEF SUMMARY OF SOME OF THE PREFERRED EMBODIMENTS

Ethylene and propylene, high volume commodity chemicals, are manufactured world wide by various methods, but one of the more common methods is the cracking of the alkane (propane/ethane) to the alkene (propylene/ethylene). Typically, cracking of ethane or propane to ethylene or propylene yields primarily ethylene or propylene, but byproducts are also formed. These byproducts include acetylene, vinyl acetylene, methyl acetylene, dienes and diacetylene. The presence of these byproducts, even in relatively small amounts, has deleterious or undesirable effects on subsequent chemical conversions. For example in polyethylene manufacture, the presence of even small amounts of acetylene in ethylene leads to excessive crosslinking, discolorization and in some cases catalyst deactivation or poisoning. Thus, it is desirable to convert the alkynes and diolefins (acetylenic and diolefinic compounds) to alkenes, but not further convert the alkenes to alkanes. Reactions of alkenes, such as ethylene, are generally more controllable than those of alkynes, such as acetylene, and diolefins such as dibutenes, which tend to create oligomers and undesirable polyfunctional compounds.

These byproducts can be removed by various means. Examples of industrially practiced methods include physical separation, distillation at low temperature, and hydrogenation of all or a part of the entire stream. Two general types of gaseous phase selective hydrogenation processes for purifying unsaturated hydrocarbons have come into use. One, known as "front-end" hydrogenation, involves passing the crude gas from the initial cracking step, after removal of steam and condensible organic matter, over a hydrogenation catalyst. The crude gas normally contains a relatively large amount of hydrogen, far in excess of that required to hydrogenate any acetylenes and sufficient in fact to hydrogenate a substantial part of the olefin present. Despite this hydrogen excess, operation with sufficient selectivity to give olefins of polymerisation quality is well established and catalyst life of many years can be obtained. In the other type, known as "tail-end" hydrogenation, the crude gas is fractionated and the resulting product streams are reacted with hydrogen in slight excess over the quantity required for hydrogenation of the highly unsaturated hydrocarbons present. The tail-end hydrogenation is less critical than front-end hydrogenation in that at the low hydrogen excess a runaway reaction is not as likely; however, there is a greater tendency for deactivation of the catalyst and formation of polymers from the highly unsaturated hydrocarbons may occur as an alternative to the hydrogenation thereof. Consequently periodic regeneration of the catalyst is required.

It is thus an object of the present invention to overcome the deficiencies of the prior art and thereby to provide an integrated, energy efficient process for converting select contaminants of olefinic gas streams to useful and economically advantageous products including the initial olefin from which the contaminants were abstracted.

It is also an object of this invention to provide a process for the selective hydrogenation of acetylene and diolefinic and acetylenic compounds wherein the acetylene and/or diolefinic and or acetylenic compounds are absorbed from a gas or liquid or mixed phase stream by use of a non-hydrocarbon absorbent liquid and thereafter the absorbent liquid which contains the acetylene or acetylenic compounds is exposed to a Group VIII catalyst co-currently with a gas stream containing at least hydrogen. It is consistent with this invention that other gas or liquid components will be present in the stream that contains acetylene or acetylenic compounds, in major or minor proportions, and that these may include but are not limited to aromatics, olefins, alkanes, water, alcohols, oxides, sulfides, and amines. It is also consistent with this invention that the non-hydrocarbon absorbents used to absorb acetylene or acetylenic compounds from the aforementioned gas stream will include but not be limited to: n-methyl-2-pyrrolidone (NMP), dimethylformamide (DMF), acetone, tetrahydrofuran (THF), dimethylsulfoxide (DMSO), monomethylamine (MMA) and chloroform and that the temperature and pressure selected for hydrogenation of the acetylene or acetylenic compounds in the polar absorbent will be selected such that the liquid absorbent does not form significant vapor.

It is also an object of this invention to obtain useful conversion of acetylene at moderate temperatures and pressures. Typically, the temperature ranges from 0° F. to 400° F. and the pressure ranges from 1 to 2000 psia, and the choice of operating conditions will vary depending on the absorbent chosen and the acetylenic compounds being hydrogenated.

It is also an object of this invention that the acetylene and/or acetylenic compounds and/or diolefinic compounds are selectively hydrogenated to ethylene or homologous ethenic compounds with minimum conversion to ethane and other saturated compounds.

It is also an object of this invention that the catalyst is chosen to operate at selected reactor conditions so that a majority of the acetylenic and diolefinic compounds are converted to monoolefins with relatively low conversion of these compounds to fully hydrogenated alkanes or oligomers or polymers.

It is also an object of this invention to provide operation of the reaction process in such a way that "run-away" temperature conditions do not occur and that temperature control is naturally enhanced. The use of these liquid absorbents acts to absorb more heat with less of a temperature rise, either at the catalyst surface or throughout the fluid phase, than a gas under most process conditions, due to a larger heat capacity per volume than the gas phase alone. These liquid absorbents also provide for improved heat transfer, as their thermal conductivity is much greater under most process conditions.

It is also an object of this invention to obtain useful conversion of acetylene and/or acetylenic compounds and/or diolefinic compounds even in the presence of carbon monoxide in excess of 1% of the non-absorbent components.

It is also an object of this invention to obtain useful conversion of acetylene and/or acetylenic compounds and/or diolefinic compounds in the presence of hydrogen equal to or in excess of that stoichiometrically required to effect the total hydrogenation of the acetylene or acetylenic compounds.

It is also an object of this invention to perform the hydrogenation of acetylene and acetylenic compounds in one or more reactors in series. Any catalyst well known to selectively hydrogenate acetylene can be employed by this invention. The group VIII metal hydrogenation catalysts are generally used and preferred. Most commonly, these are employed as supported catalysts on such materials as alumina, silica, or aluminosilicates, but may be supported as well on metal meshes or screens. Most commonly, these supports contain one or more Group VIII metals in the amount of 0.01 to 10 percent by weight. There are many formulations of such catalysts which contain other components, primarily Group I through Group VII metals which improve selectivity, conversion or yield. Alternatively, other applicable catalysts include but are not limited to nickel arsenide on alumina, ruthenium on alumina, Raney-nickel, zinc oxide and zinc sulfide. In embodiments, the supported catalyst comprises a rim catalyst comprising 0.05% to 5% by weight palladium and 0.05% to 5% by weight of a promoter selected from the group consisting of gold, silver, copper, zinc, manganese, rhenium, gallium, indium, and combinations thereof. In embodiments, the activity and selectivity of the catalyst are comparable to or improved from their levels at reaction initiation. In embodiments, the supported catalyst is a skin catalyst comprising about 0.1% to about 1.0% by weight palladium and a promoter selected from the group consisting of zinc, gallium, gold, silver, copper, indium, rhenium, and manganese.

It is also an object of this invention to perform the hydrogenation in a liquid or dispersed phase such that separation can be effected by normal means including distillation, single stage flash, multistage flash, crystallization, washing with a solvent, partitioning with a non-solvent, or a combination of these common separation means, not exclusive of less common techniques that are known to those skilled in the art.

It is also an object of this invention that the olefinic compounds formed by reaction are separated from the solvent.

It is also an object of this invention that the rich solvent containing acetylenic and diolefinic compounds is separated such that heavier or more strongly absorbed components are retained in the solvent and lighter or less strongly absorbed components are released to the gas phase in a gas/liquid separator.

It is also an object of this invention that the evolved gas phase component is optionally reabsorbed in lean solvent.

It is also an object of this invention that the separate streams are subjected to conditions in separate reactors that convert at least a portion of the contaminant in at least one of the streams to a hydrogenated form.

It is also an object of this invention that there is performed substantial removal of the acetylenic and diolefinic compounds from a stream comprising olefins by treatment of the gas stream with a solvent that preferentially absorbs acetylenic and diolefinic compounds, forming a liquid phase that is richer in acetylenic and diolefinic compounds after exposure to the gas stream. It is consistent with this invention that the stream from which the acetylenic and diolefinic compounds is removed is improved in quality. It is consistent with this invention that the acetylenic and diolefinic compounds are reacted while absorbed in the liquid solvent over a solid catalyst with a source of hydrogen at a sufficient temperature, pressure and for adequate time to convert at least some of the acetylenic and diolefinic compounds to olefinic compounds. It is also consistent with this invention that the olefin produced by reaction of the acetylenic and diolefinic compounds is added to the initial olefinic gas stream, increasing the quantity of the olefinic gas above what was originally available. It is also consistent with this invention that a gas separation and purification step is performed upstream of the solvent absorber.

It is also an object of this invention that a catalyst formulation is utilized that has stable behavior for periods of time in excess of 5 hours.

It is also an object of this invention that the used solvent is regenerated so that it can be re-used and recycled many times. It is consistent with this invention that the solvent regeneration employs a separation step where by-products of the preferred reaction can be removed and isolated for subsequent use.

It is also an object of this invention that the initial source of hydrogen to the reactor is the gas stream containing the olefin.

It is also an object of this invention that the source of hydrogen may be pure hydrogen.

It is also an object of this invention that a source of carbon monoxide is introduced to the reactor.

It is also an object of this invention that the source of carbon monoxide is wholly or partly the initial gas stream containing the olefin.

It is also an object of this invention that the gaseous products of the reactor are subjected to separation thus producing one or more streams enriched in various components such as but not exclusively hydrogen, carbon monoxide, ethylene, butene and carbon dioxide.

It is also an object of this invention that the carbon monoxide produced by gas separation may be combined with the carbon monoxide stream that serves as the primary source of the carbon monoxide.

It is also an object of this invention that the hydrogen produced by gas separation may be combined with the hydrogen stream that serves as the primary source of the hydrogen.

It is also an object of this invention that the gas phase product of the reactor is combined with the rich gas stream containing the pre-existing contaminants.

It is also an object of this invention to provide a method to remove acetylenic and diolefinic compounds from a monoolefinic stream and convert said acetylenic and diolefinic compounds into one or more monoolefinic compounds comprising: contacting the monoolefin stream which contains acetylenic and diolefinic components with an aprotic, liquid solvent in which the acetylenic and diolefinic compounds are more soluble than the olefinic components, thereby effecting separation of at least some of the acetylenic and diolefinic compounds from the monoolefinic stream, concentrating the acetylenic and diolefinic compounds in the liquid solvent to form an enriched solvent, and a lean monoolefin stream, which is reduced in acetylenic and diolefinic compounds content, introducing the enriched solvent to at least one reactor containing a catalyst comprising a Group VIII element, introducing a source of hydrogen to the at least one reactor, operating the at least one reactor at conditions sufficient to maintain a portion of the acetylenic or diolefinic compounds within the liquid phase and to hydrogenate at least a portion of the acetylenic and diolefinic compounds contained within the enriched absorbent, preferentially to monoolefins, recovering the monoolefins from the solvent such that the monoolefin product can be subjected to further purification or added to the lean monoolefin stream.

It is also an object of this invention to provide a method to remove acetylenic and diolefinic compounds from a monoolefinic stream and convert those acetylenic and diolefinic compounds into monoolefinic compounds comprising: contacting the monoolefin stream which contains acetylenic and diolefinic components with an aprotic, liquid solvent in which the acetylenic and diolefinic compounds are more soluble than the olefinic components thereby effecting at least some separation of the acetylenic and diolefinic compounds from the monoolefinic stream resulting in some concentration of the acetylenic and diolefinic compounds in the liquid solvent forming an enriched solvent and a lean monoolefin stream which is reduced in acetylenic and diolefinic compounds, introducing the enriched solvent to a reactor or reactors containing catalyst which substantially retains or exceeds its initial activity and selectivity after 5 hours of operation, introducing a source of hydrogen to the reactor or reactors, operating the reactor at such conditions sufficient to maintain a portion of the acetylenic and/or diolefinic compounds within the liquid phase and to hydrogenate at least a portion of the acetylenic and diolefinic compounds contained within the enriched absorbent, preferentially to monoolefins, recovering the monoolefins from the solvent now depleted in acetylenic compounds and/or diolefinic compounds by ordinary means such that the monoolefin product can be subjected to further purification or added to the lean monoolefin stream and the solvent can be reused in the process as lean solvent.

DETAILED DESCRIPTION OF THE PREFERRED EMBODIMENTS

Herein will be described in detail specific preferred embodiments of the present invention, with the understanding that the present disclosure is to be considered an exemplification of the principles of the invention, and is not intended to limit the invention to that illustrated and described herein. The present invention is susceptible to preferred embodiments of different forms or order and should not be interpreted to be limited to the specifically expressed methods or compositions contained herein. In particular, various preferred embodiments of the present invention provide a number of different configurations of the process.

Initially, the alkene stream can be comprised of any alkene or combination of alkenes, but preferred examples of this application will be to streams that are predominantly ethylene or propylene. Such nearly pure component streams can be created by a number of technologies, chemistries, treatments or procedures. One method, for the purpose of illustration only, used extensively in commercial production of these identified alkenes is thermal cracking of their fully hydrogenated precursor. Thus, on a commercial scale, ethane is cracked to form ethylene and propane is cracked to form propylene. Thermal or otherwise energy induced cracking typically produces a minor amount of the acetylenic and diolefinic compounds that must be removed. Various solvents have proven effective at selectively removing acetylenic and diolefinic compounds from streams of alkenes. Some of these are acetone, dimethylformamide (DMF), tetrahydrofuran (THF), dimethylsulfoxide (DMSO), n-methyl-2-pyrrolidone (NMP) and monomethylamine (MMA). One preferred method of abstracting the acetylene from the predominantly alkene stream is to pass the gas concurrently through a properly designed absorber. Typically, absorbers will contain contact plates, random packing, structured packing, liquid distributors, screens, demisters and other such accoutrements to ensure adequate contact between the rich gas (alkyne containing) and lean solvent (acetylenic and diolefinic compounds deficient) to form a rich solvent (acetylenic and diolefinic compounds content increased) and lean gas (acetylenic and diolefinic compounds reduced). The absorber is preferably operated at a temperature and pressure to economically remove acetylenic and diolefinic compounds from the rich gas stream. Higher pressure and lower temperature typically enhance gas absorption into a liquid. The upper limit on pressure is imposed by the tendency of acetylenic and diolefinic compounds to spontaneously decompose or detonate. Therefore, refrigeration may or may not be used, although operation at moderate pressures in the range of 15 psia to 1000 psia should be expected. After it is formed, the rich solvent is conveyed to a reactor containing an improved solid catalyst suitable for hydrogenation of the acetylenic and diolefinic compounds while absorbed in the solvent and providing long life, economical service. In embodiments, the catalyst is a supported catalyst comprising a rim catalyst comprising 0.05% to 5% by weight palladium and 0.05% to 5% by weight of a promoter selected from the group consisting of gold, silver, copper, zinc, manganese, rhenium, gallium, indium, and combinations thereof. In embodiments, the activity and selectivity of the catalyst are comparable to or improved from their levels at reaction initiation. In embodiments, the supported catalyst is a skin catalyst comprising about 0.1% to about 1.0% by weight palladium and a promoter selected from the group consisting of zinc, gallium, gold, silver, copper, indium, rhenium, and manganese. A source of hydrogen is also fed to the reactor. Depending upon the design of the reactor the source of hydrogen can be a gas containing hydrogen or a chemical that contains hydrogen which may be introduced as a solid, liquid or gas. The reactor is operated at a sufficient pressure and temperature to convert some of the acetylenic and diolefinic compounds to alkene, and is preferentially operated to convert all of the acetylenic and diolefinic compounds to alkene without forming substantial alkane. The exact product composition will depend on the user's requirements. Following reaction, the alkene product and solvent will be separated. Depending on the pressure and temperature at which the hydrogenation reactor is operated, this may be accomplished by flashing (single stage or multistage) to a lower pressure, distillation (single or multicolumn), extraction (single stage or multistage) or other appropriate separation techniques.

The source of hydrogen to the hydrogenation reactor may contain, be mixed with or co-fed with non-hydrogen components. These may include but are not limited to water, carbon dioxide, carbon monoxide, ammonia, various amines, ethane, ethylene, propane, propylene, acetylene and propyne. Since carbon monoxide is often utilized in low concentrations to improve selectivity of typical hydrogenation catalysts, a separate carbon monoxide stream may be provided. Significantly higher concentrations of carbon monoxide at levels which it would normally be considered a catalyst poison can be used in this reaction without detriment to the reaction product or catalyst.

Some of these constituents may not react and may exit the reactor in the liquid or the gas effluent following downstream separation. Therefore, it is expected that the effluent gas stream may be subjected to purification operations such as, but not limited to: distillation, pressure swing absorption, membrane separation and contaminant absorption by a selective solvent. It is also anticipated that the rich liquid effluent from the reactor may contain reaction by-products, catalyst fines and other non-product components. Therefore, the liquid may need to be purified or treated before being reused. Although it is possible that the solvent could be used only one time, it is much more economical to re-use the liquid repeatedly. Purification of the liquid by removing substantial portions of the contaminants may be accomplished by single units, multiple units, or combination of units including, but not restricted to: extraction, leaching, distillation, absorption, adsorption, crystallization and filtration.

Once purified, if purification is necessary, the evolved gas stream may be recombined with the lean gas stream from the absorber. The liquid, if purification is necessary, may be recirculated to the absorber column.

Performing the absorption step using a selective solvent does remove the acetylenic and diolefinic compounds from the alkene stream. Properly designed, the absorber concentrates the acetylenic and diolefinic compounds in the liquid stream many times. The more concentrated the acetylenic and diolefinic compounds, the more heat is released per volume when the acetylenic and diolefinic compounds are hydrogenated. This is a serious difficulty in gas phase reactions. High heat release per volume values are tolerated by the solvent in which the acetylenic and diolefinic compounds are dissolved because the heat capacity per volume of reactant is increased between about one and two orders of magnitude. Temperature increases are kept low and temperature control is much easier. Once a molecule of acetylenic and diolefinic compounds is converted to a molecule of alkene, the solvent's tendency to hold on to the molecule decreases significantly. Therefore, even at reaction pressure and temperature, much of the product desorbs immediately from the solvent. When the pressure of the liquid is lowered, in passing through a control valve, for example, more alkene product will evolve, making separation of the alkene from the solvent relatively simple and easy to accomplish. This evolved alkene can be immediately combined with the lean alkene from the absorber or sent to further purification to remove any non-alkene gases, depending on its purity.

Figure 1:
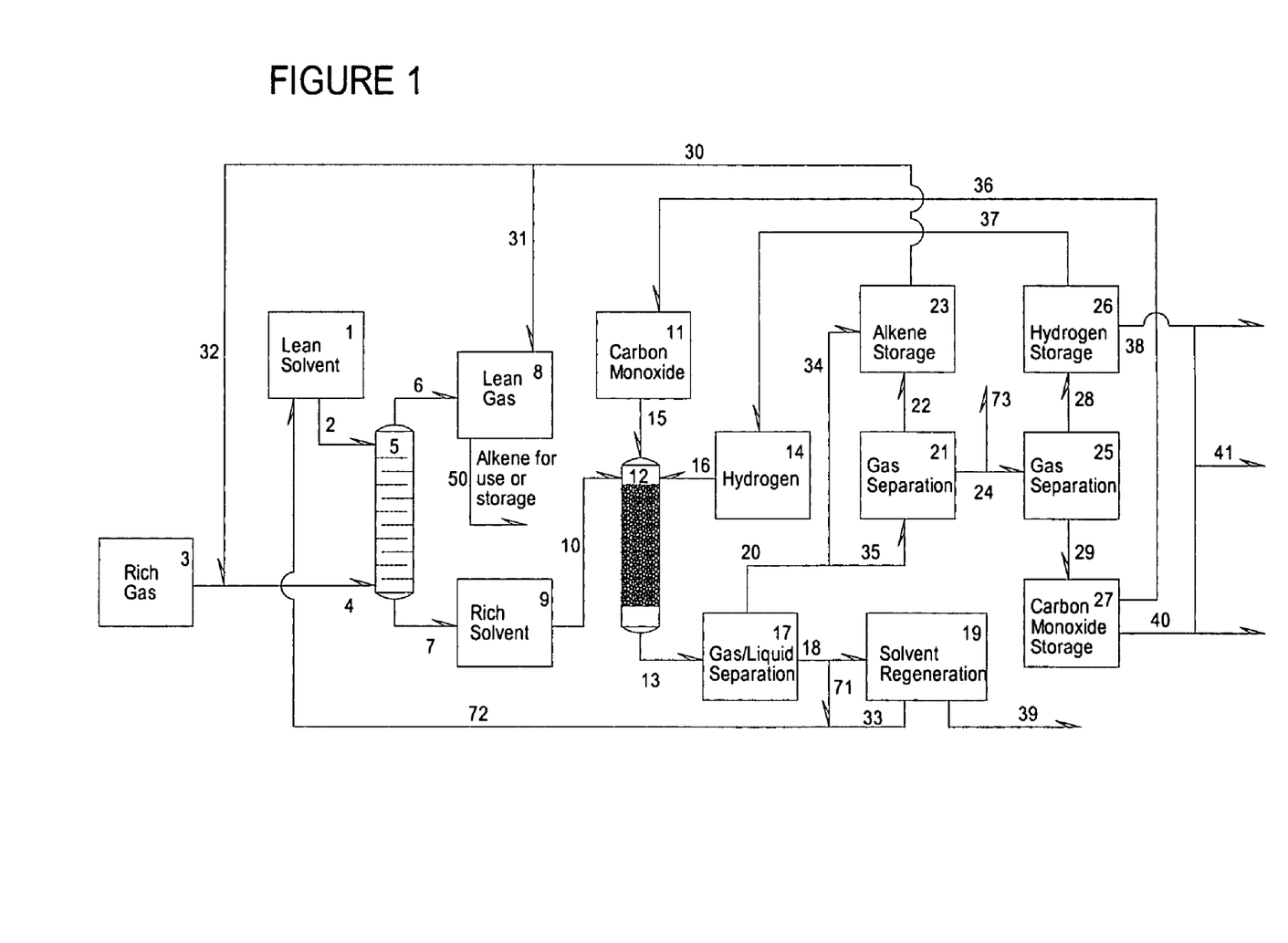
FIG. 1 is a schematic process flow diagram illustrating certain embodiments described in the present disclosure.

Referring now to FIG. 1, there are shown certain preferred embodiments for producing an improved olefin stream such as ethylene from a stream contaminated with the classes of compounds represented by acetylene, methyl acetylene, vinyl acetylene and propadiene, and hydrogenating those contaminants in order to produce the classes of compounds represented by ethylene, propylene and butene. As shown in FIG. 1, the contaminant laden rich gas stream 4 obtained from rich gas source 3 is passed counter-currently with lean solvent stream 2 obtained from lean solvent source 1, such as a storage tank, into a gas/liquid contactor 5, such as an absorber capable of producing a contaminant reduced or lean gas stream 6 and rich solvent stream 7. The term "storage" as used herein should be understood to mean permanent or temporary holdup wherein holdup time may be zero, as in the case wherein the storage device is a transfer line or part of a transfer line. The rich solvent stream 7, which may contain carbon dioxide, is conveyed to one or more reactors 12 via rich solvent 9 and line 10 and fed concurrently with stream 16 which contains at least hydrogen and optionally a stream 15 which comprises carbon monoxide. Stream 16 may contain some carbon monoxide. This mixture is passed through reactors 12 and emerges as a stream of solvent containing at least some hydrogenated product 13, which is fed to the gas/liquid separator 17, such as a flash tank. The gas/liquid separator 17 is operated at such conditions to produce a gas stream 20 which contains the desired hydrogenated monoolefin without producing significant amounts of completely hydrogenated alkanes or oligomers or polymers. Gas stream 20, depending upon composition, is optionally passed through a gas separation device 21 such as a membrane. The product olefin stream 22 is transferred to alkene storage 23 from which product stream 30 is sent by stream 31 to lean gas storage 8, or reprocessed by conveying it to rich gas storage 3 via stream 32. The remaining gas stream 24 obtained from the gas separation unit 21 can optionally be utilized in subsequent processing via stream 73 or optionally be transferred to subsequent further separation in gas separation unit 25, such as a membrane or cryogenic separation device, forming a stream rich in hydrogen 28 and a stream rich in carbon monoxide 29. The carbon monoxide rich stream can optionally be sent to a carbon monoxide storage facility 27. The hydrogen rich stream can optionally be sent to a hydrogen storage facility 26.

The absorber 5 will be operated within a nominal range of temperature from about 50° F. to 150° F. (about 10° C. to about 66° C.) and at a pressure of approximately 25 psig to about 500 psig (about 1.7 to about 34 $bar_g$). Best and most economical absorption occurs when the temperature of operation is as low as possible without refrigeration and the pressure is as high as economically possible without developing conditions that could lead to spontaneous ignition of any of the components that might detonate. The rich gas stream 4 may need to be pressurized in order to feed it to the absorber. The operating conditions of the absorber 5 will be dependent upon the concentration and identity of the contaminants in rich gas stream 4. The ability of the rich solvent 7 to contain contaminants depends upon pressure, temperature, the specific chemical identity of the contaminants contained and their concentration. The preferred operation temperature of reactor 12 will be within the range of about 100° F. to 400° F. (about 38° C. to about 204° C.). The desired operation pressure of reactor 12 will be about 50 to 500 psig (about 1.7 to 34 $bar_g$) and more preferably 100 to 250 psig (about 6.9 to 17 $bar_g$). Introduction of hydrogen, optionally carbon monoxide, and rich solvent to the reactor at the operating conditions will result in a mixture of gas and liquid being driven through the bed of catalyst if the reactor 12 is of the trickle bed type or any fixed bed type. It is not intended to operate the reactor at such conditions to vaporize a significant amount of the solvent. It is most preferable to operate the reactor at such conditions that will maintain the majority to all of the solvent in the liquid phase. The solvent and absorbed gases and co-flowing gases, some of which may be products, emerge out of the reactor outlet and form effluent stream 13, which is conveyed to the gas/liquid separator 17. The gas liquid separator is operated at the conditions necessary to produce a gas stream 20 and a liquid stream 18. If the rich gas is actually a liquid at flowing conditions, the desired physical state of the olefin product may be liquid as well. The term "gas" as it is used in "rich gas" or "lean gas" or "gas stream" is not necessarily meant to indicate the actual physical state of either olefin containing stream, but is meant to indicate the physical state of the stream under conditions of standard pressure and temperature only. Depending upon the process conditions involved, such streams may be stored, transported through, or removed from the process as liquids. If desired, the gas stream 20 may be sent immediately to alkene storage 23 via stream 34. If gas stream 20 contains other species, such as hydrogen and carbon monoxide, it may be conveyed via stream 35 to a gas separation device 21, an example being a membrane gas separator. The olefin stream 22 is sent to alkene storage 23 which thereafter may be sent via streams 30 and 31 to lean gas storage 8, such as a process line or returned via stream 30 and 32 to stream 4 for reprocessing. Lean gas accumulated in lean gas storage 8 is conveyed by stream 50 to use or alternate storage.

The non-olefin stream 24 may be vented, burned, conveyed to separate storage via line 73 or sent to gas separation unit 25, such as a membrane separator. The effluent hydrogen containing gas stream 28 can be conveyed to separate hydrogen storage 26 or immediately conveyed to reactor feed hydrogen storage 14. The effluent carbon monoxide containing gas stream 29 can be conveyed to separate carbon monoxide storage 27 or immediately conveyed to reactor feed carbon monoxide storage 11. The liquid stream 18 from gas/liquid separator 17, which is depleted in alkene content, may contain other components or waste products. All or a portion of stream 18 may be sent to solvent regeneration 19. The solvent regeneration unit 19, an example being a distillation column, is operated at the conditions necessary to produce reclaimed or regenerated solvent stream 33 and may produce a waste stream 39 composed of solids and/or liquids and or gases. All or a portion of stream 71 may be sent to lean solvent source 1 via line 72.

Hydrogen accumulated in hydrogen gas storage 26 may be sent to hydrogen supply 14 via stream 37 or sent to other uses via stream 38. Carbon monoxide in carbon monoxide storage 27 may be sent to carbon monoxide storage 11 via stream 36 or sent to other uses via stream 40. In some cases, such as for purposes of creating a fuel mixture or a reactant blend known as syngas, all or portions of these gas streams 38 and 40 may be commingled forming gas stream 41.

Figure 2:
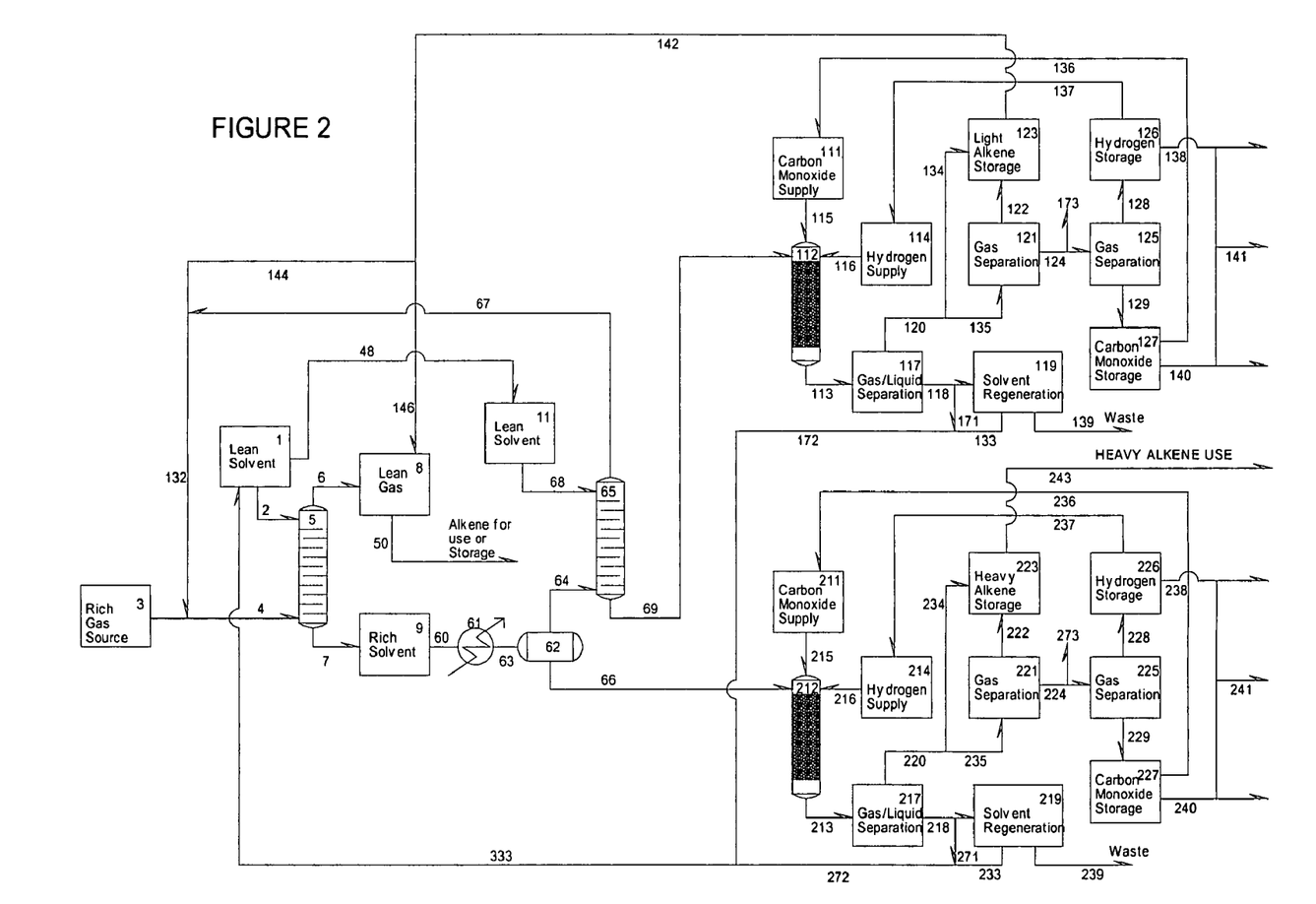
FIG. 2 is a schematic process flow diagram illustrating certain preferred embodiments described in the present disclosure.

Referring now to FIG. 2, shown therein are certain preferred embodiments for producing improved olefin streams such as ethylene and propylene from a stream contaminated with the classes of compounds represented by acetylene, methyl acetylene, vinyl acetylene and propadiene and hydrogenating those contaminants in order to produce the class of compounds represented by ethylene, propylene and butene. As shown in FIG. 2, the contaminant laden rich gas stream 4 is passed counter-currently with lean solvent stream 2 obtained from lean solvent storage 1, such as a storage tank, into a gas/liquid contactor 5, such as an absorber capable of producing contaminant reduced or lean gas stream 6 and rich solvent stream 7. The rich solvent stream 7 is conveyed to heater 61, via rich solvent 9 and line 60, where it is heated sufficiently, forming heated stream 63 in order to cause some of the absorbed contaminant absorbed in liquid stream 7 to enter the gas phase at the normal operating conditions of gas/liquid separator 62, such as a flash separator causing and resulting in partitioning of the differently absorbed components. Depending upon design or operating conditions of separator 62, heater 61 may not be needed and therefore optional equipment. By way of illustration and not limitation, the component that enters the gas phase may preferably be homologous to the component that remains in the liquid phase, but with a lower molecular weight and thus referred to as lighter. The gas stream 64 that is produced in gas/liquid separator 62 is conducted to gas/liquid contactor 65, such as an absorber. The gas/liquid contactor 65 is operated at a pressure and temperature such that when mixed with lean solvent stream 68 obtained from lean solvent storage 11, which may be fluidly connected with lean solvent storage 1 via line 48, a portion of gas stream 64 and liquid stream 68 mix to form liquid stream 69. Any portion of gas stream 64 which is not absorbed into liquid stream 69 exits gas/liquid contactor 65 as gas stream 67 which is optionally recombined via stream 132 with gas from rich gas source 3 forming rich gas stream 4.

Rich solvent 66 containing heavier or more strongly absorbed contaminants from gas/liquid separator 62 is conveyed to one or more reactors 212 and fed co-currently with at least a stream 216 which contains some hydrogen and optionally a stream 215 which comprises carbon monoxide. Stream 216 may contain some carbon monoxide. This mixture is passed through reactors 212 and emerges as a stream of solvent containing at least some hydrogenated product 213, which is fed to the gas/liquid separator 217, such as a flash tank. The gas/liquid separator is operated at such conditions to produce a gas stream 220 which contains a desired hydrogenated monoolefin without producing significant amounts of completely hydrogenated alkanes or oligomers or polymers. Gas stream 220, depending upon composition, is optionally passed via stream 234 to heavy alkene storage 223 or sent via stream 235 through a gas separation device 221, such as a membrane. The product olefin stream 222 is transferred to heavy olefin storage 223 and is sent via stream 243 to subsequent use. The remaining gas stream 224 obtained from the gas separation unit 221 can optionally be utilized in subsequent processing via stream 273 or may optionally be transferred to subsequent further separation in gas separation unit 225, such as a membrane or cryogenic separation device, forming a stream rich in hydrogen 228 and a stream rich in carbon monoxide 229. The carbon monoxide rich stream can optionally be sent to a carbon monoxide storage facility 227. The hydrogen rich stream can optionally be sent to a hydrogen storage facility 226.

Rich solvent 69 containing lighter or less strongly absorbed contaminants from gas/liquid contactor 65 is conveyed to one or more reactors 112 and fed co-currently with at least a stream 116 which contains some hydrogen and optionally a stream 115 which comprises carbon monoxide. This mixture is passed through reactors 112 and emerges as a stream of solvent containing at least some hydrogenated product 113, which is fed to the gas/liquid separator 117, such as a flash tank. The gas/liquid separator is operated at such conditions to produce a gas stream 120 which contains a desired hydrogenated monoolefin without producing significant amounts of completely hydrogenated alkanes or oligomers or polymers. Gas stream 120, depending upon composition, is optionally passed via stream 134 to light alkene storage 123 or via stream 135 through a gas separation device 121, such as a membrane. The product olefin stream 122 is transferred to light olefin storage 123 and is there after sent via stream 142 and stream 146 to lean gas storage 8 or may be combined with rich gas stream 4 for reprocessing via streams 142, 144 and 132. Lean gas accumulated in lean gas storage 8 is conveyed by stream 50 to use or alternate storage. The remaining gas stream 124 obtained from the gas separation unit 121 can optionally be utilized in subsequent processing via stream 173 or may optionally be transferred to subsequent further separation in gas separation unit 125, such as a membrane or cryogenic separation device, forming a stream rich in hydrogen 128 and a stream rich in carbon monoxide 129. The carbon monoxide rich stream can optionally be sent to a carbon monoxide storage facility 127. The hydrogen rich stream can optionally be sent to a hydrogen storage facility 126.

The absorber 5 and the absorber 65 will be operated within a nominal range of temperature from about 50° F. to 150° F. (about 10° C. to about 66° C.) and at a pressure of approximately 25 psig to about 500 psig (about 1.7 to about 34 $bar_g$). Best and most economical absorption occurs when the temperature of operation is as low as possible without refrigeration and the pressure is as high as economically possible without developing conditions that could lead to spontaneous ignition of any components that might detonate. The rich gas stream 4 may need to be pressurized in order to feed it to the absorber. The operating conditions of the absorber 5 will be dependent upon the concentration and identity of the contaminants in rich gas stream 4. The ability of rich solvents 7 and 69 to contain their respective contaminants depends upon pressure, temperature, the specific chemical identity of the contaminants contained and their concentration. The preferred operation temperature of reactors 112 and 212 will be within the range of about 100° F. to 400° F. (about 38° C. to about 204° C.). The desired operation pressure of reactors 112 and 212 will be about 50 to 500 psig (about 3.4 to about 34 $bar_g$) and more preferably 100 to 250 psig (about 6.9 to about 17.2 $bar_g$). Introduction of hydrogen, optionally carbon monoxide, and rich solvent to the reactor at the operating conditions will result in a mixture of gas and liquid being driven through the bed of catalyst if the reactors 112 or reactors 212 are of the trickle bed type or any fixed bed type. It is not intended to operate the reactors at such conditions to vaporize a significant amount of the solvent. It is most preferable to operate the reactors at such conditions that will maintain the majority to all of the solvent in the liquid phase. The solvent, and the absorbed gases and co-flowing gases, some of which may be products, emerge out of the reactor outlets and form effluent stream 113 or 213 respectively, which are conveyed to the their respective gas/liquid separators 117 or 217. The gas-liquid separators are operated at conditions necessary to produce gas streams 120 and 220 and liquid streams 118 and 218, respectively. Depending upon the components, gas streams 120 and/or 220 may contain the desired olefin or the liquid streams 118 and/or 218 may contain the desired olefin.

The respective liquid streams 118 and 218 from respective gas/liquid separators 117 and 217, which are depleted in alkene content, may contain other components or waste products. All or a portion of streams 118 and 218 may be sent, respectively, to solvent regeneration 119 and 219. The respective solvent regeneration units 119 and 219, example being distillation columns, are operated at the conditions necessary to produce respectively reclaimed or regenerated solvent streams 133 and 233 and respectively may produce waste streams 139 and 239, either or both composed of solids and/or liquids and or gases. All or a portion of streams 118 and 218 may be transferred to lean solvent sources 1 and 11 via streams 171 and 271 respectively, and thereafter via streams 172 and 272 respectively to stream 333. Streams 133 and 233 may be sent via streams 172 and 272 respectively to be combined to form stream 333, returning regenerated or reclaimed solvent to lean solvent storage 1 for recycle.

If the rich gas stream 4 is actually a liquid at flowing conditions, the desired physical state of the olefin product may be liquid as well. The term "gas" as it is used in "rich gas" or "lean gas" or "gas stream" is not necessarily meant to indicate the actual physical state of either olefin containing stream, but is meant to indicate the physical state of the stream under conditions of standard pressure and temperature only. Depending upon the process conditions involved, such streams may be stored, transported through, or removed from the process as liquids. If the gas streams 120 and/or 220 consist of only the desired olefin product, gas stream 120 may be sent immediately to light alkene storage 123 and gas stream 220 may be sent to heavy alkene storage 223. If either gas stream 120 or 220 contains other species, such as hydrogen and carbon monoxide, either may be conveyed to its respective gas separation device 121 or 221, an example being membrane gas separators. Thereupon, the olefin stream 122 is sent to light alkene storage 123 and the olefin stream 222 is sent to heavy alkene storage 223. All or portions of the non-olefin streams 124 and 224 may be vented, burned, conveyed to separate storage or use via streams 173 and 273, respectively, the remaining portions thereof being sent to their respective gas separation units 125 or 225, such as membrane separators. The effluent hydrogen containing gas streams 128 or 228 can be conveyed respectively to separate hydrogen storage 126 or 226 or immediately conveyed respectively to reactor feed hydrogen storage 114 or 214 by respective stream 137 or 237. The effluent carbon monoxide containing gas streams 129 and 229 can be conveyed respectively to separate carbon monoxide storage 127 or 227 or immediately conveyed respectively to reactor feed carbon monoxide storage 111 or 211 respectively by streams 136 or 236.

Hydrogen accumulated in hydrogen gas storage 126 or 226 may be sent respectively to hydrogen supply 114 or 214 via respective streams 137 or 237 or respectively sent to other uses via streams 138 or 238. Carbon monoxide in carbon monoxide gas storage 127 or 227 may be sent respectively to carbon monoxide supply 111 or 211 via respective streams 136 or 236 or respectively sent to other uses via stream 140 or 240. In some cases, such as for purposes of creating a fuel mixture or a reactant blend known as syngas, all or portions of these gas streams 138 with 140 and 238 with 240 may be respectively co-mingled forming gas stream 141 or 241.

The examples provided in the disclosure are presented for illustration and explanation purposes only and are not intended to limit the claims or embodiments of this invention. While the preferred embodiments of the invention have been shown and described, modification thereof can be made by one skilled in the art without departing from the spirit and teachings of the invention. Process design criteria, pendant processing equipment, and the like for any given implementation of the invention will be readily ascertainable to one of skill in the art based upon the disclosure herein.

The embodiments described herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

Use of the term "optionally" with respect to any element of the invention is intended to mean that the subject element is required, or alternatively, is not required. Both alternatives are intended to be within the scope of the invention.

The discussion of a reference in the Description of the Related Art is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

We claim:

1. A method to remove acetylenic and diolefinic compounds from a monoolefinic stream and convert said acetylenic and diolefinic compounds into one or more monoolefinic compounds comprising:

contacting the monoolefin stream which contains acetylenic and diolefinic components with an aprotic, liquid solvent in which the acetylenic and diolefinic compounds are more soluble than the olefinic components, thereby effecting separation of at least some of the acetylenic and diolefinic compounds from the monoolefinic stream, concentrating the acetylenic and diolefinic compounds in the liquid solvent to form an enriched solvent, and a lean monoolefin stream, which is reduced in acetylenic and diolefinic compounds content, introducing the enriched solvent to at least one reactor containing a supported catalyst comprising a Group VIII element, co-currently introducing a gas stream comprising at least hydrogen to the at least one reactor, operating the at least one reactor at conditions sufficient to maintain a portion of the acetylenic or diolefinic compounds within the liquid phase and to hydrogenate at least a portion of the acetylenic and diolefinic compounds contained within the enriched absorbent, preferentially to monoolefins, producing a reactor product stream comprising solvent, monoolefins and at least one selected from the group consisting of hydrogen and carbon monoxide, separating the reactor product stream into a solvent stream and a monoolefin product stream comprising monoolefins and at least one selected from the group consisting of hydrogen and carbon monoxide, introducing the monoolefin product stream into a first gas separation device configured to separate a monoolefin-enriched stream from a monoolefin-reduced stream, wherein the monoolefin-reduced stream comprises at least one selected from the group consisting of hydrogen and carbon monoxide, introducing the monoolefin-reduced stream into a second gas separation device configured for separation of hydrogen, carbon monoxide, or both from the monoolefin-reduced stream, and recycling at least one selected from the separated hydrogen and the separated carbon monoxide to the at least one reactor.

2. The method of claim 1 wherein the aprotic liquid solvent is selected from the group consisting of dimethylformamide, hexamethylphosphoramide, N-methylpiperidone, n-methylpyrrolidone, dimethylacetamide, sulfolane, acetone, dimethylsulfoxide, tetrahydrofuran, chloroform, and combinations thereof, and the monoolefin stream comprises a component selected from the group consisting of ethylene, propylene, 1-butene, 2-butene, and combinations thereof.

3. The method of claim 1 wherein the supported catalyst comprises a rim catalyst comprising 0.05% to 5% by weight palladium and 0.05% to 5% by weight of a promoter selected from the group consisting of gold, silver, copper, zinc, manganese, rhenium, gallium, indium, and combinations thereof, and the activity and selectivity of the catalyst are comparable to or improved from their levels at reaction initiation.

4. The method of claim 1 further comprising co-currently introducing a stream comprising carbon monoxide to the at least one reactor to improve the hydrogenation results, wherein the molar ratio of hydrogen to alkyne and diolefin added to the reactor is within the range of from about 1:1 to about 5:1, the molar ratio of carbon monoxide to hydrogen is within the range of from about 1:1 to about 1:100, the reactor temperature is in the range of from about 100° F. to about 400° F., the reactor pressure is in the range of from about 1 psig to about 1000 psia.

5. The method according to claim 1 wherein the supported catalyst comprises about 0.5% by weight palladium, gallium, and from about 0.05% to about 0.35% by weight zinc.

6. A method to remove acetylenic and diolefinic compounds from a monoolefinic stream and convert those acetylenic and diolefinic compounds into monoolefinic compounds comprising:

contacting the monoolefin stream which contains acetylenic and diolefinic components with an aprotic, liquid solvent in which the acetylenic and diolefinic compounds are more soluble than the olefinic components thereby effecting at least some separation of the acetylenic and diolefinic compounds from the monoolefinic stream resulting in some concentration of the acetylenic and diolefinic compounds in the liquid solvent forming an enriched solvent and a lean monoolefin stream which is reduced in acetylenic and diolefinic compounds, introducing the enriched solvent to at least one reactor containing a supported catalyst which substantially retains or exceeds its initial activity and selectivity after 5 hours of operation wherein the supported catalyst comprises about 0.5% by weight palladium, gallium, and from about 0.05% to about 0.35% by weight zinc, co-currently introducing a stream comprising hydrogen and a stream comprising carbon monoxide to the at least one reactor, operating the at least one reactor at conditions sufficient to maintain a portion of the acetylenic and/or diolefinic compounds within the liquid phase and to hydrogenate at least a portion of the acetylenic and diolefinic compounds contained within the enriched absorbent to hydrogenation product monoolefins, recovering from the at least one reactor an outlet stream comprising the hydrogenation product monoolefins, hydrogen, carbon monoxide, and solvent, and separating a monoolefin product stream comprising the hydrogenation product monoolefins, hydrogen and carbon monoxide from the solvent to produce a lean solvent stream.

7. The method of claim 6 wherein the supported catalyst is a skin catalyst.

8. The method of claim 6 where the aprotic liquid solvent comprises a compound known to absorb acetylenic compounds preferentially to ethylenic compounds selected from the group consisting of dimethylformamide, hexamethylphosphoramide, N-methylpiperidone, n-methylpyrrolidone, dimethylacetamide, sulfo lane, acetone, dimethylsulfoxide, tetrahydrofuran, chloroform, and combinations thereof.

9. The method of claim 8 wherein the liquid solvent is dimethylformamide, n-methyl-pyrrolidone, or dimethylsulfoxide.

10. The method of claim 9 wherein the liquid solvent is n-methyl-pyrrolidone.

11. The method of claim 6 wherein the amount of carbon monoxide introduced into the at least one reactor is adjusted to provide a molar ratio of carbon monoxide to hydrogen of between 1:1 and 1:100.

12. The method of claim 6 further comprising conveying the monoolefin product stream comprising hydrogenation product monoolefins, hydrogen and carbon monoxide to a gas separator and substantially separating the hydrogenation product monoolefins from a remaining gas stream comprising carbon monoxide and hydrogen.

13. The method of claim 12 further comprising subjecting the remaining gas stream to gas separation, thus forming a hydrogen-enriched stream and a carbon monoxide-enriched stream, and recycling the hydrogen-enriched stream, the carbon monoxide-enriched stream, or both to the at least one reactor.

14. The method of claim 6 wherein the enriched solvent comprises a plurality of acetylenic and diolefinic compounds having different absorptivities in the solvent.

15. The method of claim 14 further comprising removing, at least in part, one or more of the plurality of acetylenic and diolefinic compounds from the enriched solvent to the gas phase.

16. The method of claim 15 wherein the enriched solvent is heated to an adequate temperature and controlled at a pressure whereby a portion of the acetylenic and diolefinic compounds form a gas phase stream.

17. The method according to claim 16 wherein the gas phase stream is reabsorbed into lean solvent.

18. The method according to claim 17 wherein the re-absorbed gas phase stream is subjected to hydrogenation and subsequent alkene processing separately from the liquid solvent stream from which it was abstracted.

19. A method to remove contaminants selected from acetylenic and diolefinic compounds from a gaseous feedstream comprising monoolefins and convert at least some of those contaminants into monoolefinic compounds, the method comprising:

(a) contacting the gaseous feedstream with an aprotic, liquid solvent in which the contaminants are more soluble than the monoolefins to form a first enriched solvent and a lean monoolefin gas stream, wherein the first enriched solvent comprises aprotic, liquid solvent and at least some of the contaminants and wherein the lean monoolefin gas stream is reduced in contaminants relative to the gaseous feedstream, (b) partitioning the first enriched solvent into a light gas phase stream and a heavy solvent stream, wherein the light gas phase stream comprises relatively lighter contaminants than the contaminants in the heavy solvent phase, (c) absorbing the light gas phase stream into lean aprotic, liquid solvent to form a second enriched solvent, (d) co-currently introducing the second enriched solvent and a gas stream comprising hydrogen or co-currently introducing the second enriched solvent, a gas stream comprising hydrogen and another gas stream comprising carbon monoxide into a first hydrogenation reactor containing a supported catalyst comprising a Group VIII element and operating the first hydrogenation reactor at conditions sufficient to maintain a portion of the contaminants therein within the liquid phase and to hydrogenate at least a portion of the contaminants contained within the second enriched solvent to light monoolefins, producing a first hydrogenation reactor product comprising light monoolefins and solvent, (e) separating the light monoolefins from the solvent, providing a first recovered solvent, (f) co-currently introducing the heavy solvent stream and a gas stream comprising hydrogen or co-currently introducing the heavy solvent stream, a gas stream comprising hydrogen and another gas stream comprising carbon monoxide into a second hydrogenation reactor containing a supported catalyst comprising a Group VIII element and operating the second hydrogenation reactor at conditions sufficient to maintain a portion of the contaminants therein within the liquid phase and to hydrogenate at least a portion of the contaminants contained within the heavy solvent stream to heavy monoolefins, and (g) separating the heavy monoolefins from the solvent, providing a second recovered solvent.

20. The method of claim 19 further comprising recycling the first recovered solvent, the second recovered solvent, or both to (a), (c), or both.

* * * * *